United States Patent [19]

Greenwood et al.

[11] Patent Number: 4,950,240
[45] Date of Patent: Aug. 21, 1990

[54] HYPODERMIC SYRINGE FOR SINGLE USE

[76] Inventors: Eugene C. Greenwood, 2956-B Pepper Tree La., Costa Mesa; John A. Holland, 1836 Port Abbey Pl., Newport Beach, both of Calif. 92660

[21] Appl. No.: 334,312

[22] Filed: Apr. 6, 1989

Related U.S. Application Data

[63] Continuation-in-part of Ser. No. 253,137, Oct. 4, 1988.

[51] Int. Cl.⁵ .............................................. A61M 5/00
[52] U.S. Cl. ..................................... 604/110; 604/228
[58] Field of Search ................ 604/110, 218, 187, 228

[56] References Cited

U.S. PATENT DOCUMENTS 4,775,363 10/1988 Sandsdalen ........................ 604/110
4,775,364 10/1988 Alles .................................. 604/110

Primary Examiner—John D. Yasko
Attorney, Agent, or Firm—Roy A. Ekstrand

[57] ABSTRACT

A single use hypodermic syringe uses a generally cylindrical elongated syringe body defining a center bore and supporting a hollow needle in communication with the center bore. A movable piston preferably formed of rubber or resilient plastic material is sealingly supported within the syringe bore. A driver member extends into the syringe bore and is coupled to the piston by a coupling which features upon a single use. Several embodiments of the single use coupling are shown which fraction to preclude any further use of the syringe once the fluid injection operation has been implemented by the syringe.

7 Claims, 3 Drawing Sheets

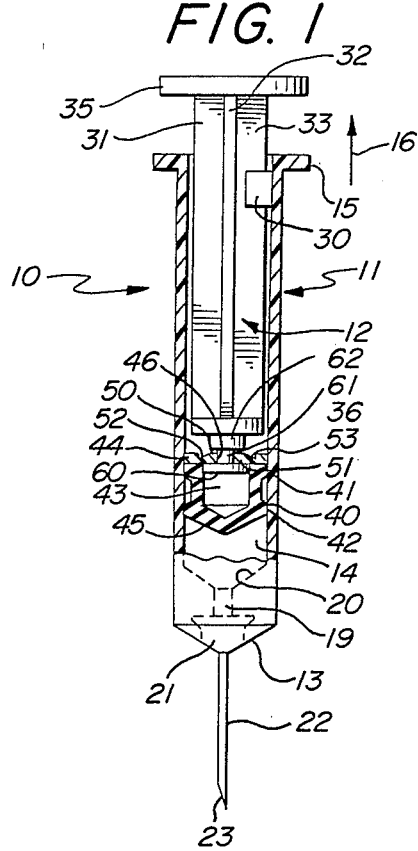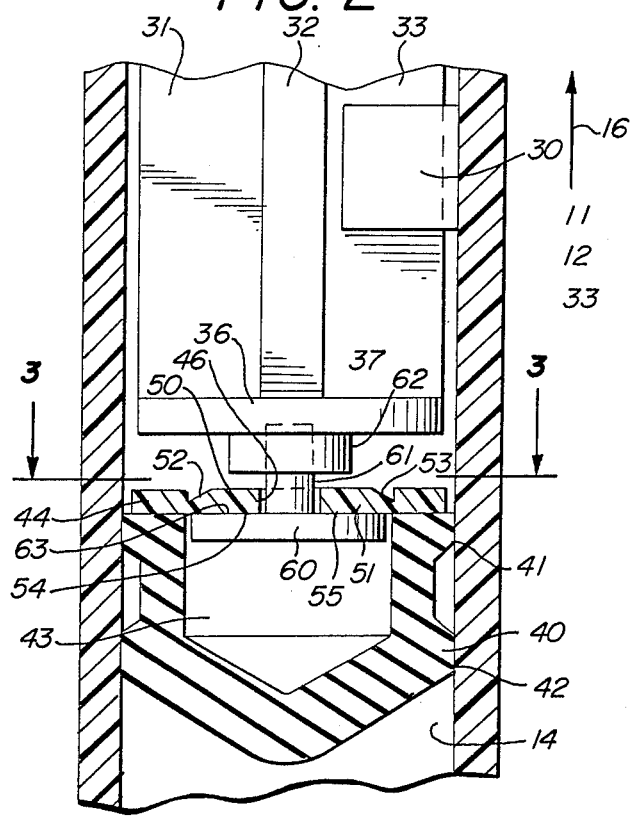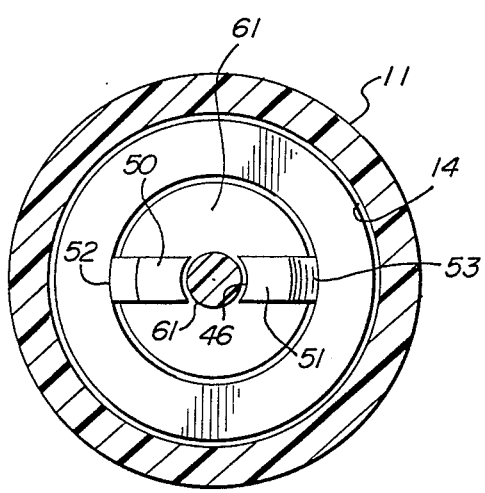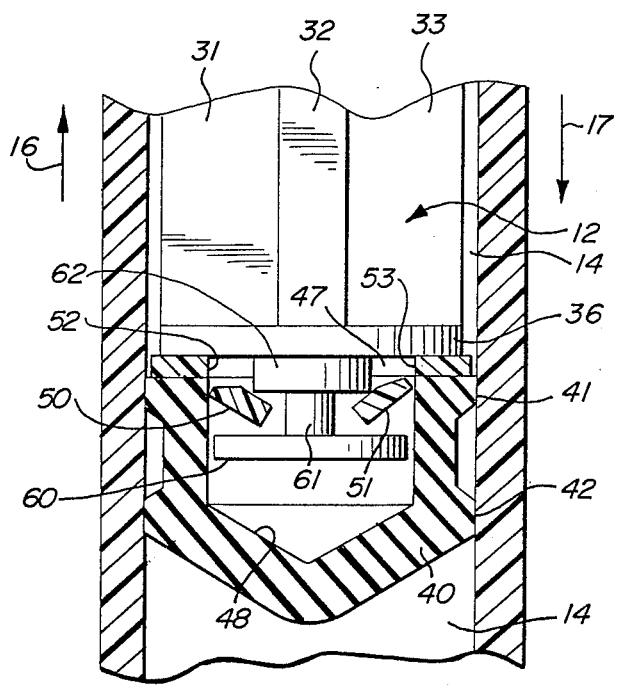

HYPODERMIC SYRINGE FOR SINGLE USE

CROSS REFERENCE TO RELATED PATENT APPLICATIONS

This application is a continuation-in-part of copending application serial number 07/253,137 filed Oct. 4, 1988 and entitled SINGLE USE SYRINGE which was filed in the name of the applicants of this application.

FIELD OF THE INVENTION

This invention relates generally to hypodermic syringes and particularly to a mechanism by which such hypodermic syringes are incapable of multiple use.

BACKGROUND OF THE INVENTION

In the medical arts, one of the more commonplace devices is the hypodermic syringe which is used to inject a quantity of fluid beneath the skin of a patient. While the structures of such hypodermic syringes vary with design choice, all generally include a cylindrical barrel defining a central cylindrical bore which terminates at one end in a restricted passage in communication with an outwardly extending hollow pointed needle. The remaining end is generally open and receives a piston assembly which includes an elongated driver supporting a piston. The piston is sized to sealingly slide within the bore of the syringe barrel and thereby control the volume confined within the interior of the syringe bore between the end needle passage and the piston.

In typical use, the needle is inserted into a small container after which the piston driver is drawn outwardly from the syringe barrel moving the piston away from the needle passage and drawing a quantity of the to-be-injected fluid into the syringe bore. Thereafter, the needle is withdrawn from the container and the syringe is pointed upwardly. The piston driver is then moved into the syringe bore a short distance to expel any trapped air from the syringe interior making the syringe ready for use. As a final step, the needle is inserted into or beneath the skin of the patient and the driver is moved inwardly within the syringe bore to expel the desired quantity of fluid into the patient's system. Finally, the needle is withdrawn from the patient's skin and discarded.

While syringes manufactured and used by the medical profession today are generally intended for a single use, in fact their structures are often sufficiently sturdy to facilitate multiple use by persons obtaining them through various unauthorized means. Most prevalent among such unauthorized users of hypodermic syringes are intravenous drug users who often use such syringes repeatedly and in many cases exchange syringes with fellow intravenous drug users.

While a problem of infection and disease proliferation has usually accompanied such unauthorized use of syringes by intravenous drug users, the recent increase in the disease known as Acquired Immune Deficiency Syndrome (AIDS) has greatly increased the alarm of the medical profession at such unauthorized use of discarded syringes.

Through the years, a number of hypodermic syringes have been developed which are directed to increasing the safety of use of hypodermic syringes. One such device is set forth in U.S. Pat. No. 3,306,290 issued to Weltman which sets forth an AUTOMATICALLY RETRACTABLE NEEDLE SYRINGE having an elongated tubular body defining a central bore and a slidable piston assembly therein. A hub mounted on the body portion defines an axial bore, receives the needle portion of the syringe and provides a safety member therefor.

U. S. Pat. No. 4,258,713 issued to Wardlaw sets forth an AUTOMATIC DISPOSABLE HYPODERMIC SYRINGE in which a disposable syringe includes a retracted needle which is driven by a spring to administer an injection. The needle is contained within a housing and is driven from the housing to administer the injection. A release mechanism is provided to operate the syringe.

U.S. Pat. No. 4,188,950 issued to Wardlaw sets forth a DISPOSABLE SYRINGE in which provisions are made for rendering the needle incapable of harming anyone once the unit is discarded. The syringe operates with a retracted needle which is driven to a protruding position when the device is used. After use the needle is retracted from the protruding position and is bent to prevent the needle from harming anyone and to prevent reuse of the needle.

U.S. Pat. No. 4,189,009 issued to Alvarez sets forth a HYPODERMIC NEEDLE ASSEMBLY WITH RETRACTABLE NEEDLE COVER in which a disposable hypodermic needle assembly includes a permanently attached but retractable covering means for the forward portions of the needle. The covering means include an annular slide member slidable with respect to the needle and normally positioned to cover the forward or pointed portion of the needle. A plurality of elastically resilient arms support the slide member in the covering position but may be withdrawn therefrom by sliding the slide member down the needle shaft and overcoming the elasticity of the resilient arms. Once the needle is used, the resilient arms return the slide member to the covering position and means are provided for locking the slide member in the covering position.

U.S. Pat. No. 4,507,117 issued to Ryan, et al. sets forth a SYRINGE APPARATUS WITH RETRACTABLE NEEDLE in which a syringe apparatus includes a syringe barrel and internal movable piston as well as an extending needle portion in communication therewith. A first locking member locks the needle in the extended position while a second locking member locks the needle to the slidable piston within the syringe barrel. In use, the needle is initially locked in the extending position and injection is administered. Thereafter, the needle may be unlocked from the extended position and retracted into the barrel by locking the needle to the piston and drawing the piston inwardly pulling the needle into the barrel interior.

U.S. Pat. No. 4,378,015 issued to Wardlaw sets forth an AUTOMATIC INJECTING SYRINGE in which a hypodermic needle employs a retracted needle contained within the syringe housing. The syringe is fabricated from a minimum number of parts and is intended to be inexpensively and easily assembled. A safety feature is included which prevents accidental operation of the syringe.

U.S. Pat. No. 4,775,864 issued to Alles sets forth a NONREUSEABLE DISPOSABLE HYPODERMIC SYRINGE in which a hypodermic needle includes an elongated cylindrical barrel having a closed end supporting a hypodermic needle and an open end. An elongated plunger rod extends into the cylindrical bore and is coupled to a movable rubber plunger. The plunger defines a plurality of outwardly extending rib portions forming sealing engagement with the interior of the cylindrical barrel. The cylindrical barrel defines an inwardly extending annular ring which receives and captures the plunger when the plunger is driven forwardly of the extending ring. A portion of the plunger rod defines a narrowed cross sectional member designed to break when the plunger rod is drawn outwardly with the plunger captivated within the annular ring.

U.S. Pat. No. 4,775,863 issued to Sandsdalen sets forth an ARRANGEMENT IN INJECTION SYRINGE FOR USE ONCE ONLY in which a hypodermic syringe includes an elongated cylindrical barrel portion defining an open end and a closed end supporting a hypodermic needle. An elongated piston rod extends into the cylindrical bore from the open end and supports a plurality of claw members extending toward the closed end. A movable piston is sealingly movable within the cylindrical bore of the syringe barrel and defines an inclined surface and an annular ring portion. The claws on the piston rod are configured to engage the annular ring on the outside surface of the piston during the first drawing stroke permitting fluid to be aspirated into the syringe barrel interior as the piston is drawn outwardly. Once the piston is forced forward to expel the aspirated fluid through the needle, the expelling force exerted upon the piston rod causes the claws to be disconnected by the inclined surface on the piston rendering the syringe incapable of further use.

While the foregoing described prior art devices provide some protection and increased safety of the use of hypodermic syringes and some prevention of the reuse thereof, they often render the hypodermic syringe more costly to manufacture and more cumbersome to use. In addition, several of the prior art structures, such as those described above intended to render the hypodermic syringe limited to a single use, require a special action on the part of the medical professional to assure the non-reuse of the hypodermic syringe. The need for additional manipulation of the syringe to render it incapable of further use imposes an undesirable burden on the medical professional and raises the possibility of reusable syringes being available.

There remains, therefore, a need in the art for a convenient to use, inexpensive to manufacture hypodermic syringe which is limited to a single use. There remains a further need for such a single use syringe which is automatically rendered inoperative following its normal use by the medical professional.

SUMMARY OF THE INVENTION

Accordingly, it is a general object of the present invention to provide an improved hypodermic syringe. It is a more particular object of the present invention to provide an improved hypodermic syringe designed for a single use. It is a still more particular object of the present invention to provide an improved hypodermic syringe for single use which is automatically rendered inoperable following its first use.

In accordance with the invention, there is provided a single use syringe having an elongated syringe body supporting a movable piston therein and coupled to a hypodermic needle. A driver extends into the interior of the syringe body and is coupled to the interior of the piston by coupling means which render the syringe inoperable once the piston has been driven forward within the syringe body.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIG. 1 sets forth a partially sectioned side view of a hypodermic syringe constructed in accordance with the present invention;

FIG. 2 sets forth a partial section view of a hypodermic syringe constructed in accordance with the present invention during the outward drawing stroke of the piston;

FIG. 3 sets forth a cross section view of the present invention hypodermic syringe taken along section lines 3—3 in FIG. 2;

FIG. 4 sets forth a partial section view of the present invention hypodermic syringe at the initiation of a forward stroke of the piston;

DESCRIPTION OF THE PREFERRED EMBODIMENTS

Figure 5:
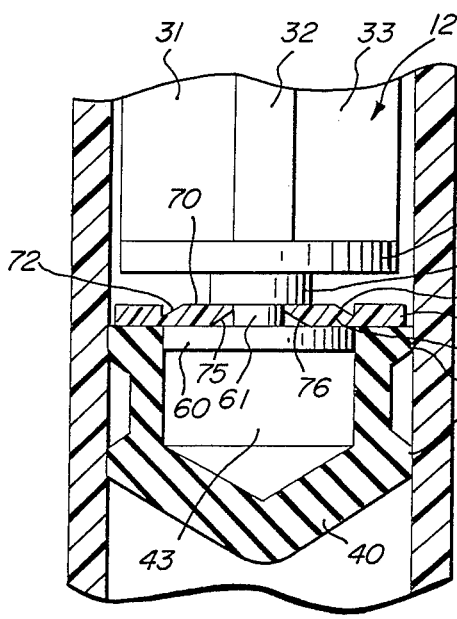
FIG. 5 sets forth a partial section view of the present invention hypodermic syringe during the forward stroke of the piston.

FIG. 1 sets forth a partial section view of a hypodermic syringe 10 constructed in accordance with the present invention. Syringe 10 includes an elongated generally cylindrical syringe body 11 defining a flange 15 at one end and a taper 13 at the other end. Syringe body 11 further defines an interior generally cylindrical syringe bore 14 extending from flange 15 to a funnel end 20 proximate taper 13. A needle retainer 21 is supported within syringe body 11 proximate taper 13 and in turn supports an elongated hollow needle 22 defining a point 23. A passage 21 defined within syringe body 11 extends from funnel end 20 to needle retainer 21 and provides communication between needle 22 and bore 14. A piston 40, preferably formed of a resilient rubber material or the like, defines a pair of outwardly extending rib seals 41 and 42 which form sealing contact with the interior of bore 14. Piston 40 further defines an interior cavity 48. A beam plate 44 having a generally planar annular structure is fitted within bore 14 and is attached to piston 40 Beam plate 44 further defined a center aperture 46 and a pair or inwardly extending beam members 50 and 51. A pair of fulcrums 52 and 53 join beam members 50 and 51 respectively to beam plate 44.

A driver 12 is formed of a quartet of outwardly extending rib members 31, 32, 33 and 34 (the latter not shown). Ribs 31 through 34 are commonly joined and generally perpendicularly arranged to provide an elongated rigid driver capable of supporting substantial compressive forces. Driver 12 further defines a knob 35 and an end flange 36 at opposite ends of ribs 31 through 34. A breaker ring 62 extends downwardly from end flange 36 and forms a generally cylindrical extension thereof. A retractor shaft 61 having a diameter smaller than aperture 46 of beam plate 44 extends from breaker ring 62 through aperture 46 to the interior of cavity 43 of piston 40. A generally planar cylindrical retractor head 60 is joined to retractor shaft 61 within cavity 43. Thus, retractor head 60 is captivated within cavity 43 by beam plate 44 and beams 50 and 51 and is joined to breaker ring 62 by retractor shaft 61.

An inwardly extending lock member 80 extends into the interior of bore 14 of syringe body 11 and is positioned between ribs 32 and 33. In its preferred form, lock member 30 may comprise a heat-formed inwardly facing protuberance of syringe body 11. The function of lock member 30 is to captivate driver 12 within syringe bore 14 of syringe body 11 while still permitting the axial movement of driver 12 within bore 14. This precludes tampering with the syringe and inactivating its self-destruct mechanism prior to using it. Accordingly, lock 30 is positioned between ribs 32 and 33 in a noninterfering alignment which permits driver 12 to be drawn outwardly from syringe body 11 until end flange 36 contacts lock member 30. Thereafter, further outward movement of driver 12 is precluded by the interference of end flange 36 and lock member 30.

In operation, hypodermic syringe 10 is initially assembled with piston 40 positioned at the bottom of bore 14 such that cone surface 45 is in contact with funnel end 20. In the assembled position, driver 12 is coupled to piston 40 by the captivation of retractor head 60 within cavity 43 by beam plate 44. In accordance with conventional operation of hypodermic syringes, point 23 of needle 22 is inserted into a contained having the to-be-injected fluid therein. Once point 23 of needle 22 is beneath the surface of the to-be-injected fluid, knob 35 of driver 12 is drawn outwardly in the direction indicated by arrow 16 which in turn brings retractor head 60 into contact with the undersides of beam 50 and 51. In accordance with an important aspect of the present invention, the planar configuration of retractor head 60 and the extended diameter of retractor head 60 cooperate to apply the force applied to beam members 50 and 51 close to fulcrums 52 and 53 respectively. As is described below in greater detail, the application of force by retractor head 60 to beams 50 and 51 close to fulcrums 52 and 58 respectively couples the force through very short lever arms for the force. This permits piston 40 to be drawn upwardly within bore 14 without breaking beams 50 or 51. In accordance with the preferred fabrication of the embodiment of the present invention shown in FIG. 1, beam plate 44 is constructed of a brittle material such as acrylic. Once piston 40 has been drawn upwardly within bore 14 of syringe body 11, the to-be-injected fluid is drawn into the interior of bore 14.

Thereafter, with the desired volume of to-be-injected fluid supported within bore 14 and captivated by piston 40, syringe 10 is withdrawn from the container and reoriented such that needle 22 points upwardly and driver 12 is moved into syringe body 11 a short distance to expel any trapped air within bore 14 and the interior of hollow needle 22. Once the trapped air has been expelled, point 23 of needle 22 is forced through the patient's skin to the desired interior portion of the patient's anatomy and driver 12 is forced inwardly with respect to syringe body 11 which in turn drives piston 40 downwardly within bore 14 and forces the captivated fluid outwardly from bore 14 through needle 22 to accomplish the desired injection.

By means set forth below in greater detail, the forward stroke of driver 12 which moves piston 40 downwardly causes breaker ring 62 to break beam 50 and 51. With beams 50 and 51 broken, retractor head 60 is moved downwardly within cavity 43 of piston 40 and end flange 36 contacts beam plate 44 and thereafter couples the downward force of driver 12 to piston 40.

In accordance with an important aspect of the present invention, however, once the foregoing sequence of operations has occurred resulting in the severing or breaking of beam members 50 and 51, any attempt to draw piston 40 outwardly within bore 14 results in simple pulling retractor head 60 through beam plate 44 which because of the previous severing of beams 50 and 51 offers no resistance to retractor head 60 permitting it to simply be withdrawn from piston 40. Thus, by the foregoing operation, driver 12 is no longer operatively coupled to piston 40 and syringe 10 is rendered inoperative.

FIG. 2 sets forth a section view of a portion of hypodermic syringe 10 during the above-described drawing motion of piston 40. Accordingly, syringe 10 defines a cylindrical body 11 having a cylindrical bore 14 therein and supporting an inwardly extending lock member 30. Piston 40 is sealingly supported within bore 14 by a pair of outwardly extending seal members 41 and 42. Piston 40 defines a generally cylindrical interior cavity 48 and is preferably formed of a resilient rubber material or the like. A generally planar annular beam plate 44 is preferably formed of a brittle material such as acrylic and is configured to easily fit within bore 14. Beam plate 44 further defines a pair of inwardly extending beam members 50 and 51 defining an aperture 46 therebetween and joined to beam plate 44 at a pair of fulcrum points 52 and 53 respectively. Beam plate 44 further defines an aperture 47 (better seen in FIG. 4). In accordance with an important aspect of the present invention, aperture 47 is slightly larger than the diameter of cavity 43.

Driver 12 comprises a quartet of elongated generally rectangular ribs 31, 32, 33 and 34 (the latter not shown) arranged in a mutually perpendicular relationship. Driver 12 further defines a generally cylindrical end flange 36 joined to ribs 31 through 34 and a generally cylindrical breaker ring 62. In accordance with an important aspect of the present invention, breaker ring 62 defines a cross section substantially smaller than cavity 43 but larger than aperture 46 between beams 50 and 51. A retractor head 60 defines a generally planar cylindrical member having a cross section slightly smaller than cavity 43 together with a generally cylindrical retractor shaft 61 extending upwardly from retractor head 60 through aperture 46. Retractor shaft 61 is received and secured within recess 37 of drive 12 to provide a secure attachment between retractor head 60 and driver 12.

In the position shown in FIG. 2, driver 12 is being drawn upwardly in the direction indicated by arrow 16 at the initiation of the above-described filling operation of bore 14. As mentioned above, the drawing motion of driver 12 causes surface 63 of retractor head 60 to be pulled against surfaces 54 and 55 of beam members 50 and 51 respectively. In accordance with an important aspect of the present invention, the application of force between retractor head 60 and beams 50 and 51 close to fulcrum 62 and 53 respectively applies a bending moment to beams 50 and 51 through short lever arms which beams 50 and 51 can sustain. Accordingly, drawing motion of driver 12 causes beam plate 44 to withstand the force coupled by retractor head 60 and permits beam plate 44 and piston 40 to be drawn upwardly in the direction of arrow 16 within bore 14 of syringe body 11.

FIG. 3 sets forth a cross section view of the embodiment of FIG. 2 taken along section lines 3—3. Cylindrical syringe body 11 defines an interior bore 14 within which an annular beam plate 44 is received. As described above, beam plate 44 defines a center aperture 47 and a pair of inwardly extending beam members 50 and 51. Beam members 50 and 51 define an aperture 46 therebetween. Beam members 50 and 51 are joined to beam plate 44 at a pair of fulcrum points 52 and 53 respectively. Retractor head 60, defining a generally cylindrical planar member, is captivated beneath beam members 50 and 51 and defines an upwardly extending cylindrical retractor shaft 61 which extends between beam members 50 and 51 through aperture 46.

FIG. 4 sets forth a partial section view of hypodermic syringe 10 showing the position of driver 12, retractor head 60, and piston 40 at the initiation of a downward stroke of driver 12 to cause the fluid within bore 14 to be expelled as described above. The downward motion of driver 12 in the direction indicated by arrow 17 forces breaker ring 62 against beam members 50 and 51. Because the diameter of breaker ring 62 is substantially less than that of retractor head 60, the forces in the direction of arrow 17 against beam members 50 and 51 are applied a substantial distance from fulcrums 52 and 53 respectively. As a result, the reduced diameter of breaker ring 62 causes the downward force to be applied to beam members 50 and 51 through longer lever arms which impose greater bending moments upon the beams. Accordingly, with the downward force applied to beam members 50 and 51 by breaker ring 62, the beam members are unable to support the greater bending moments of the applied forces and fracture at fulcrums 52 and 53 respectively causing beam members 50 and 51 to be broken from the remainder of beam plate 44. In the position shown in FIG. 4, this breakage of beam members 50 and 51 has just occurred and the continuing downward motion of driver 12 in the direction indicated by arrow 17 will bring retractor head 60 into contact with tapered surface 48 of cavity 43. Thereafter, the force applied by driver 12 to piston 40 via disk 44 causes a corresponding downward motion of piston 40 which in turn expels the captivated fluid within bore 14 in accordance with the above-described operation.

At the completion of the downward stroke, the fluid captivated within bore 14 has been expelled and beam members 50 and 51 are completely severed from beam plate 44. In accordance with an important aspect of the present invention, a subsequent drawing motion of driver 12 in the direction indicated by arrow 16, which would otherwise cause a corresponding drawing motion upwardly of piston 40, is no longer effective because of the absence of the beam members 50 and 51. As a result, any drawing motion of driver 12 in the direction indicated by arrow 16 subsequent to a downward motion in the direction indicated by arrow 17 simply withdraws retractor shaft 61 and retractor head 60 from the interior of cavity 43 through aperture 47 in beam plate 44. Thus, piston 40 remains fixed at the bottommost portion of bore 14 (better considered by examination of FIG. 1). As a result, the present invention syringe 10 is rendered completely inoperative once beam members 50 and 51 have been broken and syringe 10 is incapable of further use as piston 40 remains immovably lodged at the bottommost portion of bore 14.

FIG. 5 sets forth an alternate embodiment of the present invention single use syringe which is generally identical to the embodiment set forth in FIGS. 1 through 4 in that a generally cylindrical syringe body 11 defines a cylindrical bore 14 and a driver 12 constructed in accordance with the above-described driver structure defines a flange 36 and a quartet of support ribs 31 through 34. Piston 40 is constructed in accordance with the above-described embodiment and defines a pair of seal members 41 and 42 and an interior cavity 43. In further accordance with the above-described embodiment, the embodiment of FIG. 5 includes a generally planar cylindrical retractor head 60 joined to breaker ring 62 by a retractor shaft 61. Retractor head 60, retractor shaft 61, and breaker ring 62 are substantially identical in the embodiment of FIG. 5 to that set forth in the embodiment of FIGS. 1 through 4 with the exception that retractor shaft 61 is somewhat shorter in the embodiment of FIG. 5. A beam plate 74, formed of a brittle material such as acrylic, defines a generally planar annular member having a pair of inwardly extending beam members 70 and 71. Beam members 70 and 71 are joined to beam plate 74 at a pair of fulcrums 72 and 73. Beam members 70 and 71 further define a pair of angled surfaces 75 and 76 respectively. As can be seen by comparison of FIG. 5 and FIG. 2, the structure of beam plate 74 is substantially the same as that of beam plate 44 with the exception of angled surfaces 75 and 76.

The operation of the alternate embodiment of FIG. 5 is substantially the same as that described above for the embodiment shown in FIGS. 1 through 4 with the exception that beams 70 and 71 are captivated between breaker ring 62 and retractor head 60 On the drawing stroke, no bending moments are applied to beams 70 and 71 due to this captivation. Thus, the beams are able to sustain the drawing force On the downward stroke, however, angled surfaces 75 and 76 of beam members 70 and 71 respectively permit beams 70 and 71 to bend between retractor head 60 and breaker ring 62. In essence, the presence of angled surfaces 75 and 76 provides a clearance for the pivotal motion of beam members 70 and 71 during the downward stroke which results in a force application through longer level arms breaking beams 70 and 71 in the manner shown in FIG. 4. In all other respects, the operation of the alternate embodiment shown in FIG. 5 is identical to that described above for the embodiment shown in FIGS. 1 through 4.

Figure 6:
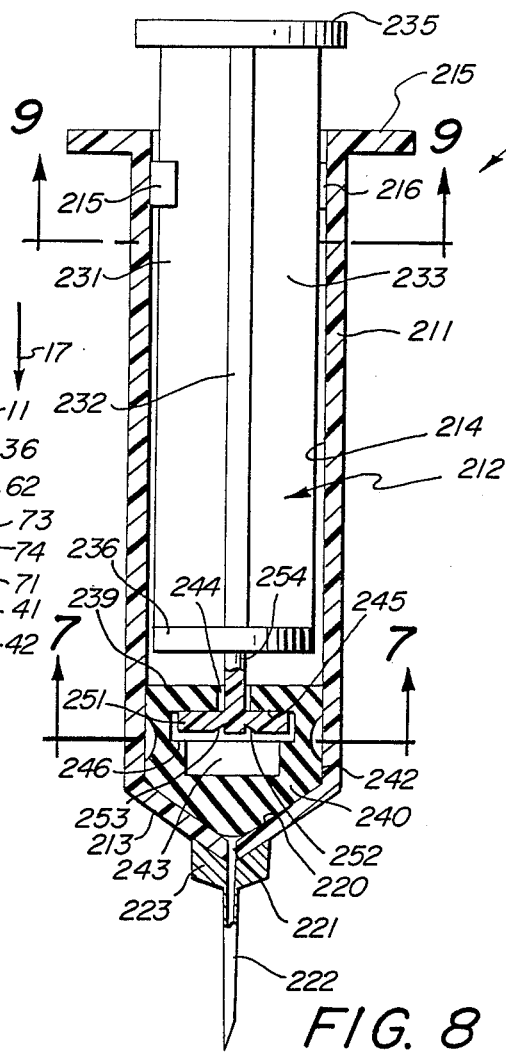
FIG. 6 sets forth a partial section view of an alternate embodiment of the present invention hypodermic syringe.

FIG. 6 sets forth an alternate embodiment of the present invention single use syringe which makes use of a different coupling mechanism between the driver and piston assembly. A hypodermic syringe generally referenced by numeral 210 includes an elongated cylindrical syringe body 211 defining an interior cylindrical bore 214, a tapered portion 213 and an outwardly extending flange 215. Syringe bore 214 tapers to a funnel end 220 at taper 213 and terminates in an outwardly extending passage 221. A needle retainer 223 is secured to taper 213 of syringe body 211 by conventional fabrication means and supports an outwardly extending hollow needle 222. In accordance with conventional fabrication techniques, the interior bore of needle 221 is communicated to syringe bore 214 by passage 221 in a sealing manner. Syringe body 211 further defines a pair of inwardly extending lock tabs 215 and 216.

Figure 9:
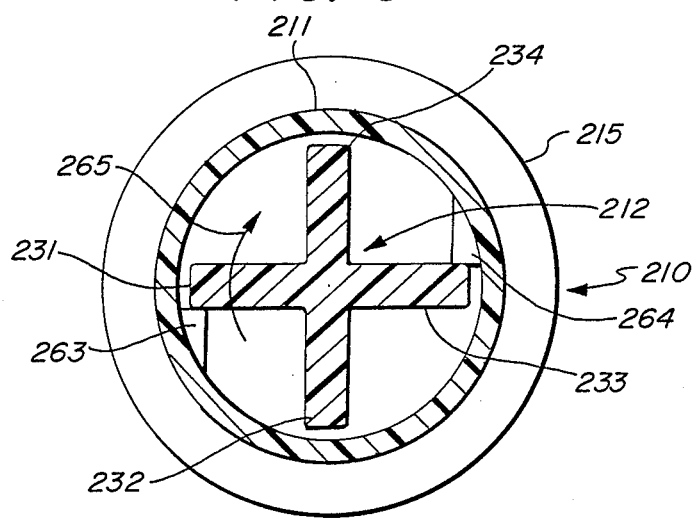
FIG. 9 sets forth a cross section view of the alternate embodiment of FIG. 8 taken along section lines 9—9 in FIG. 6.

An elongated driver 212 comprises a quartet of mutually perpendicular generally rectangular ribs 231, 232, 233 and 234 (the latter seen in FIG. 9). Ribs 231 through 234 are mutually joined to form an elongated rigid structure. Driver 212 terminates at one end in a generally planar knob 235 and at the other end in an end flange 236. Driver 212 further defines a generally cylindrical shaft 254 joined to and extending from end flange 236. Shaft 254 terminates in a pair of outwardly extending beam members 250 and 251. Beams 250 and 251 are joined to shaft 254 at a pair of reduced cross-section fulcrum points 252 and 253 respectively. In accordance with the above-described fabrication techniques, fulcrum points 252 and 253 define fracture points at which beams 250 and 251 may be severed from shaft 254 in the operation of the present invention hypodermic syringe.

A piston 240 preferably formed of a resilient material such as rubber or the like defines a generally cylindrical member having a pair of outwardly extending rib seal portions 241 and 242. Rib seals 241 and 242 are sized to be sealingly received within syringe bore 214 while permitting piston 240 to be movable within the syringe bore. Piston 240 further defines an interior cavity 248 and an aperture 244. Interior cavity 243 further defines a surface 245 extending from aperture 244 and a surface 246 generally parallel to surface 245. In accordance with the invention, shaft 214 extends through aperture 244 and supports beam members 250 and 251 within interior cavity 248 of piston 240 between surfaces 245 and 246. It should be noted that in the preferred fabrication of syringe 210, driver 212, shaft 254, and beams members 250 and 251 are integrally molded of single common molded part. Beams 250 and 251 are inserted within cavity 243 by stretching flange 239 to enlarge aperture 244 of piston 240 prior to assembly of driver 212 and piston 240 within syringe bore 214. It should also be noted that FIGS. 8 and 9 set forth below describe an alternate means of assembling beam members 250 and 251 within cavity 248 of piston 240 using a twist lock type assembly.

The operation of syringe 210 is substantially in accord with the operation of the above-described embodiments in that beam members 250 and 251 are supported within piston 240 to permit driver 212 to draw piston 240 outwardly for one aspiration or withdrawing stroke and are fractured during the forward stroke of drive 212 expelling the aspirated fluid through needle 222.

Specifically, with syringe 210 in an position shown in FIG. 6, driver 212 is drawn outwardly from syringe bore 14 by an upward motion which is coupled by shaft 254 to beam members 250 and 251. The drawing force imparted to beam members 250 and 251 is imparted thereby to flange 289 drawing piston 240 upwardly to increase the volume within syringe bore 214. During this drawing stroke, the to-be-aspirated fluid is drawn through needle 222 and passage 221 into the interior of syringe bore 214. The extent of outward motion of driver 212 is limited by a pair of inwardly extending lock tabs 215 and 216. Lock tabs 215 and 216 are formed within syringe bore 214 subsequent to assembly of driver 212 and piston 240 therein. Lock tabs 215 and 216 extend a sufficient distance into syringe bore 214 to contact end flange 236 of driver 212 and preclude its further withdrawal. Once the drawing stroke of driver 212 is completed and the desired quantity of fluid is supported within syringe bore 214, driver 212 is driven downwardly within syringe bore 214. The downward force on driver 212 is coupled to shaft 254 and to beam members 250 and 251. Because of the friction created between rib seals 241 and 242 of piston 240 against the interior of syringe bore 214, piston 240 initially resists the downward force exerted by beam members 250 and 251. This force is coupled between beam members 250 and 251 and flange 239 within interior cavity 243. Because of the increased lever arm created between flange 239 and beam members 250 and 251, the beam members fracture at fulcrums 252 and 253 respectively. With beam members 250 and 251 separated from shaft 254, the downward force of driver 212 is applied against flange 239 of piston 240 causing it to be forced downwardly within syringe bore 214. As a result, piston 240 is driven toward taper 213 causing the fluid within syringe bore 214 to be expelled.

In accordance with an important aspect of the present invention, the separation of beam members 250 and 251 destroys the coupling between shaft 254 and piston 240 rendering driver 212 incapable of withdrawing piston 240 from the end of syringe bore 214. This in turn renders syringe 210 incapable of further use.

Figure 7:
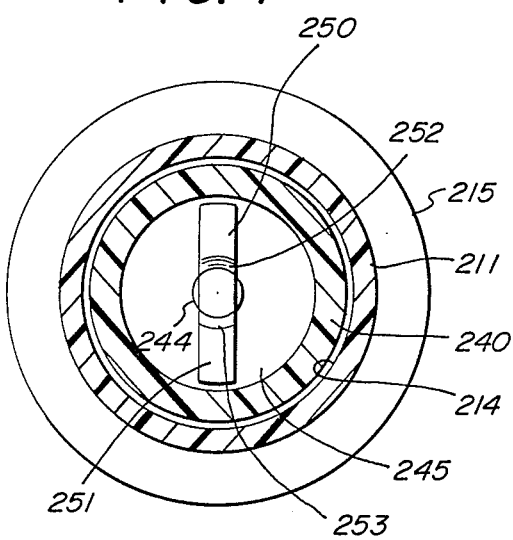
FIG. 7 sets forth a cross section view of the present invention hypodermic syringe taken along section lines 7—7 in FIG. 6.

FIG. 7 sets forth a section view of syringe 210 taken along section lines 7—7 in FIG. 6. Syringe 210 defines a cylindrical syringe body 211 which in turn defines a cylindrical interior bore 214 and an outwardly extending flange 210. Piston 240 is received within cylindrical bore 214 and defines an interior cavity 243, an aperture 244 are a flange 239. A shaft 254 extends through aperture 244 and supports a pair of outwardly extending beam members 250 and 251 at a pair of fulcrum junctions 252 and 258 respectively. As can be seen in FIG. 7, beam members 250 and 251 are captivated within cavity 243 of piston 240. It should be noted that, while the embodiment shown in FIGS. 6 and 7 utilizes a pair of radially extending beam members 250 and 251, the present invention hypodermic syringe may be fabricated utilizing a different number of beam members. For example, a single beam member such as beam member 250 joined at fulcrum 252 to shaft 254 may in some applications be sufficient to provide the desired operation of the present invention hypodermic syringe. Conversely, in other applications, an increased number of beam members may be utilized without departing from the spirit and scope of the present invention.

Figure 8:
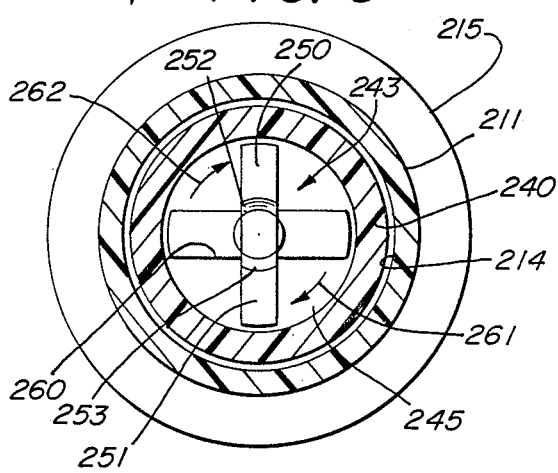
FIG. 8 sets forth a cross section view of an alternate embodiment of the present invention hypodermic syringe taken along section lines 7—7 in FIG. 6.

FIG. 8 sets forth a section view of an alternate embodiment of the syringe shown in FIG. 6 taken along section lines 7—7 therein. As will be apparent, the embodiment of FIG. 8 is virtually identical to the embodiment of FIG. 7 with the addition of an elongated slot 260 formed in surface 245 of piston 240. In accordance with an alternate embodiment of the present invention, slot 260 permits the assembly of beam members 250 and 251 within interior cavity 248 of piston 240 using a twist lock assembly process. Specifically, slot 260 extends laterally across surface 245 and is larger than the combined structures of beams 250 and 251 and shaft 254. Thus, beam members 250 and 251 are assembled to piston 240 by initially rotating driver 212 and thereby beam members 250 and 252 until beam members 250 and 251 are aligned with slot 260. Thereafter, beam members 250 and 251 may be passed through slot 260 until they clear surface 245 of piston 240. Thereafter, rotation of driver 212 and beams 250 and 251 in the direction indicated by arrows 261 and 262 captivates beam members 250 and 251 within interior cavity 243. Once the above-described assembly has taken place, the operation of the embodiment of FIG. 8 is carried forward and functions in virtual agreement with the above-described embodiment shown in FIGS. 6 and 7.

Figure 12:
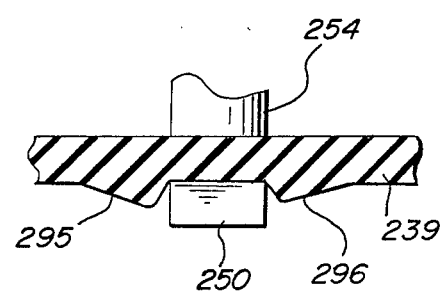
FIG. 12 sets forth a partial section view of an alternate embodiment of the present invention hypodermic syringe.

FIG. 9 sets forth a section view of the alternate embodiment of the present invention shown in FIG. 8 taken along section lines 9—9 in FIG. 6. Syringe body 211 defines a cylindrical member having an interior cylindrical bore 214 and an outwardly extending flange 215. As described above, driver 212 defines a quartet of mutually perpendicular ribs 281, 232, 233 and 234. Syringe body 211 further defines a pair of inwardly extending lock tabs 268 and 264. Lock tabs 263 provide the same function as set forth above for lock tabs 215 and 216 in FIG. 6 in that they preclude driver 212 from being withdrawn from syringe bore 214 once assembly is complete. However, in accordance with the twist lock assembly of the embodiment of FIG. 8, lock tabs 263 and 264 provide tapered lock surfaces which permit driver 212 to be rotated only in the direction indicated by arrow 265. As driver 212 is rotated in the direction indicated by arrow 265, the tapered structures of lock tabs 263 and 264 as well as the resilience of the materials from which syringe body and ribs 231 through 234 are formed, permits ribs 231 through 234 to be forced past lock tabs 263 and 264 in the direction indicated by arrow 265. With temporary reference to FIGS. 8 and 9 together, it should be noted that the rotation of driver 212 is undertaken to provide the above-described assembly of beam members 250 and 251 within cavity 243 of piston 240 once beam members 250 and 251 have been passed through slot 260. It should be further noted that while a pair of lock tabs 268 and 264 are shown in FIG. 9, any numbers of mechanisms which restrain the rotational motion of driver 212 within syringe bore 214 may be utilized to realize the advantages of assembly of the embodiment shown in FIGS. 8 and 9. An alternative locking mechanism for preventing rotation of driver 212 is set forth in FIG. 12. Shaft 254 supports beams 250 and 251 within piston 240 against flange 239. A pair of inclined lock wedges 295 and 296 maintain beam 250 in a fixed position resulting in a twist lock function.

Figure 10:
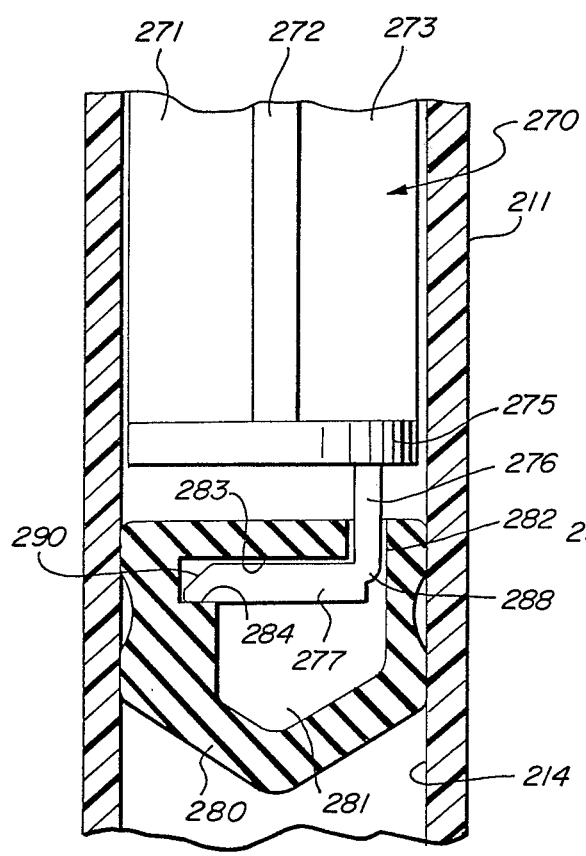
FIG. 10 sets forth a partial section view of another alternate embodiment of the present invention hypodermic syringe at the beginning of a forward piston stroke.
Figure 11:
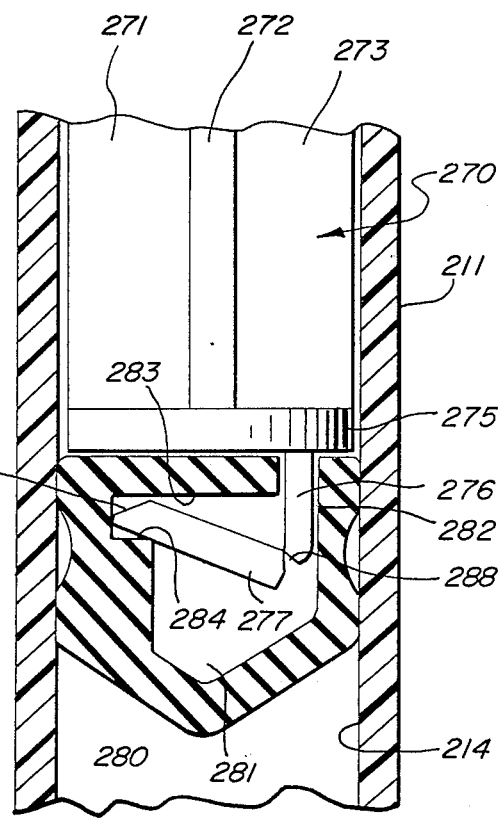
FIG. 11 sets forth a partial section view of the alternate embodiment of the present invention hypodermic syringe of FIG. 10 during a forward piston stroke.

FIGS. 10 and 11 set forth a still further alternate embodiment of the present invention in which syringe body 211 is identical to the structure shown in FIG. 6. A driver 270 includes a quartet of rectangular elongated ribs 271, 272, 273 and 274 (the latter not shown). In similar structure to driver 212 set forth above, ribs 271 through 274 are joined in a mutually perpendicular structure. Driver 270 terminates in a generally cylindrical end flange 275. A shaft 276 extends outwardly from end flange 275 and is offset from the center line of driver 270. A beam member 277 is joined to shaft 276 in a perpendicular attachment at junction 288. Beam 277 defines an angled end surface 290.

A piston 280 having an outward configuration corresponding to piston 240 set forth above defines an interior cavity 281 and an aperture 282. Cavity 281 further defines a surface 283 and a surface 284.

With specific reference to FIG. 10 in the position therein, beam 277 is assembled within cavity 281 of piston 280 by stretching aperture 282 and passing beam 277 and shaft 276 therethrough. Beam 277 is captivated within cavity 281 between surfaces 283 and 284 in the position shown in FIG. 10. During the above-described drawing stroke of driver 270, the drawing force applied to driver 270 is coupled by shaft 276 to beam 277 by junction 288. Beam 277 is supported against surface 283 which in turn couples the drawing force to piston 280 causing it to move within syringe bore 214. Thus, piston 280 and driver 270 may be drawn upwardly within syringe bore 214 to draw a quantity of fluid into the syringe interior. Once the desired quantity of fluid has been drawn into the interior or syringe bore 214, driver 270 is forced downwardly within syringe bore 214.

FIG. 11 sets forth the operation of the embodiment of the present invention shown in FIG. 10 during the initial downward motion of driver 270. The frictional forces between piston 280 and syringe bore 214 cause piston 280 to initially resist the downward force applied by shaft 276 and beam 277. This initial downward force is coupled from beam 277 to piston 280 solely by the contact of beam 277 against surface 284. The resulting lever arm created between the point of contact of beam 277 and surface 284 causes junction 288 to fracture in the manner shown in FIG. 11. This fracturing of junction 288 is further enhanced by the presence of angled surface 290 on beam 277 permitting it to pivot in the manner shown in FIG. 11. Once junction 288 has fractured, piston 280 is driven downwardly within cylindrical bore 214 by the force coupling between end flange 275 and piston 280. Once the downward stroke of piston 280 is complete and the fluid within syringe bore 214 is expelled, driver 270 is incapable of withdrawing piston 280 due to the separation of beam 277 from shaft 276. Thus, the syringe is incapable of additional use.

In each of the embodiments shown, the frictional characteristics of the piston against the inside of the syringe body bore and the strengths of the coupling mechanism between the piston and the driver to drawing and injecting forces are matched to provide breakage only in response to injecting forces.

What has been shown is a convenient inexpensive and easy to use hypodermic syringe which is constructed to preclude use after its initial operation. Several embodiments have been shown which are operative to sever the coupling between the driver member and the piston to leave the piston fixed at the bottom of the syringe bore and preclude any subsequent use.

While particular embodiments of the invention have been shown and described, it will be obvious to those skilled in the art that changes and modifications may be made without departing from the invention in its broader aspects. Therefore the aim in the appended claims is to cover all such changes and modifications as fall within the true spirit and scope of the invention.

That which is claimed is:

1. A hypodermic syringe for single use comprising:
   an elongated syringe body defining an interior syringe bore;
   a hollow needle supported by said syringe body in communication with said syringe bore;
   a piston sealingly fitted within said syringe bore defining an interior cavity and an aperture in communication therewith, said piston being movable within said syringe bore in a first direction away from said needle and a second direction toward said needle:

a piston driver extending into said syringe bore defining an end flange, a shaft member extending into said cavity through said aperture, and a beam member fracturably joined to said shaft member and captivated within said interior cavity, said piston driver, said shaft member and said beam member being formed of a single unitary molded part, said beam members fracturing and separating from said shaft when said piston driver is moved in said second direction.

2. A hypodermic syringe as set forth in claim 1 wherein said shaft member is generally centered on said end flange a plurality of beam members extend radially outwardly from said shaft member and are fracturably joined thereto.

3. A hypodermic syringe as set forth in claim 1 wherein said shaft member is joined to said end flange substantially offset from the center thereof.

4. A hypodermic syringe as set forth in claim 2 wherein said piston aperture defines an elongated slot and said piston defines twist lock means permitting said driver to be rotated within said syringe bore solely in a single direction.

5. A hypodermic syringe as set forth in claim 4 wherein said piston driver defines a plurality of rib portions and wherein said twist lock means include at least one wedge-shaped member extending into said syringe bore cooperating with said rib portions.

6. A hypodermic syringe as set forth in claim 2 wherein said syringe body includes a projection extending inwardly from said syringe body within said syringe bore, said projection cooperating with said end flange to prevent withdrawal of said driver from said syringe bore.

7. A hypodermic syringe as set forth in claim 2 wherein said piston aperture defines an elongated slot and wherein said syringe further includes twist lock means permitting said driver to be rotated within said syringe bore solely in a single direction.

* * * * *